United States Patent [19]

Kormann et al.

[11] Patent Number: 5,723,680
[45] Date of Patent: Mar. 3, 1998

US005723680A

[54] PREPARATION OF ALDEHYDES

[75] Inventors: Claudius Kormann, Bingen; Heinz-Josef Kneuper, Mannheim, both of Germany

[73] Assignee: BASF Aktiengesellschaft, Ludwigshafen, Germany

[21] Appl. No.: 817,600

[22] PCT Filed: Nov. 16, 1995

[86] PCT No.: PCT/EP95/04506

§ 371 Date: Apr. 18, 1997

§ 102(e) Date: Apr. 18, 1997

[87] PCT Pub. No.: WO96/16012

PCT Pub. Date: May 30, 1996

[30] Foreign Application Priority Data

Nov. 17, 1994 [DE] Germany ............... 44 40 801.3

[51] Int. Cl.$^6$ ................................................ C07C 45/00
[52] U.S. Cl. ................. 568/455; 568/454; 568/451; 568/483
[58] Field of Search .................. 568/451, 454, 568/455, 483

[56] References Cited

U.S. PATENT DOCUMENTS

| | | |
|---|---|---|
| 3,228,881 | 1/1966 | Thomas . |
| 3,984,478 | 10/1976 | Homeier . |
| 4,400,547 | 8/1983 | Dawes . |
| 5,387,719 | 2/1995 | Kneuper et al. ............ 568/455 |

FOREIGN PATENT DOCUMENTS

| | | |
|---|---|---|
| 26 04 545 | 8/1977 | European Pat. Off. . |
| 27 640 | 4/1981 | European Pat. Off. . |
| 33 38 340 | 5/1984 | European Pat. Off. . |
| 145 235 | 6/1985 | European Pat. Off. . |
| 244 616 | 11/1987 | European Pat. Off. . |
| 588 525 | 3/1994 | European Pat. Off. . |
| 35 00 471 | 7/1986 | Germany . |
| 36 19 746 | 12/1987 | Germany . |
| 82/03856 | 11/1982 | WIPO . |
| 94/20554 | 9/1994 | WIPO . |

OTHER PUBLICATIONS

New Syntheses with carbon monoxide, Springer Verlag, 1980, pp. 97–100.
New Syntheses with carbon monoxide, Springer Verlag, 1980, pp. 38–40.
Chem. Ber. 102, 2238–2240 (1969).
New Syntheses with carbon monoxide, Springer Verlag, 1980, pp. 55–57.
Tetrahedron Lts. No. 29, pp. 3261–3266, 1968, Pergamon Press.
Oxo with Rhodium Catalysts, Cornils et al., Jun. 1975.
Industrielle Organische Chemie, Verlag Chemie, 1978, p. 82.
Jorl. of Magnetism and Magnetic Materials 85 (1990) 285–289, Roath et al.

*Primary Examiner*—Gary Geist
*Assistant Examiner*—Screeni Padmanabhan
*Attorney, Agent, or Firm*—Keil & Weinkauf

[57] ABSTRACT

Aldehydes and/or alcohols are prepared by the hydroformylation of olefins of more than 3 carbon atoms by means of a bare rhodium catalyst dissolved homogeneously in the reaction medium, at superatmospheric pressure and at elevated temperatures, and separation of the rhodium catalyst from the liquid reaction mixture, by a process in which a magnetizable, inorganic pigment coated with a polymeric binder is used for separating the homogeneously dissolved, bare rhodium catalyst from the hydroformylation medium, and this pigment, after it has been laden with the rhodium contained in the hydroformylation medium, is separated from the liquid hydroformylation medium by applying an external magnetic field.

11 Claims, No Drawings

PREPARATION OF ALDEHYDES

This is the U.S. National Stage Application of PCT/EP95/04506 filed Nov. 16, 1995 now WO/96/16012 published May 30, 1996.

The present invention relates to a process for the preparation of aldehydes and/or alcohols by the hydroformylation of olefins of more than 3 carbon atoms by means of a bare rhodium catalyst homogeneously dissolved in the reaction medium, at superatmospheric pressure and at elevated temperatures, and separation of the rhodium catalyst from the liquid reaction mixture.

The hydroformylation of olefins with carbon monoxide and hydrogen in the presence of transition metal catalysts is known. While α-olefins can be very readily hydroformylated using rhodium-containing, phosphine-modified catalysts (cf. J. Falbe, Ed: New Syntheses With Carbon Monoxide, Springer, Berlin 1980, page 55 et seq.), this catalyst system is not very suitable for internal olefins and internal branched olefins nor for olefins with more than 7 carbon atoms (cf. Falbe, page 95 et seq.). Thus, internal carbon-carbon double bonds are hydroformylated only very slowly in the presence of such a catalyst. Since the hydroformylation product is as a rule separated by distillation from the catalyst dissolved homogeneously in the reaction system and the boiling point of the aldehyde formed in the hydroformylation increases with increasing number of carbon atoms and chain length to temperatures at which the rhodium-containing catalyst decomposes, this hydroformylation method is uneconomical for the hydroformylation of olefins of more than 7 carbon atoms. In the hydroformylation of polymeric olefins, for example of polyisobutene, the catalyst containing a noble metal cannot be recovered in reusable form.

On the other hand, internal olefins and internal branched olefins can advantageously be hydroformylated using bare rhodium, ie. rhodium compounds which are dissolved homogeneously in the hydroformylation medium and are not modified with phosphorus-containing ligands, such as phosphines or phosphites. Such rhodium catalysts which have not been modified with phosphines or phosphites and their usefulness as a catalyst for the hydroformylation of the abovementioned classes of olefins are known (cf. Falbe, page 38 et seq.). The terms bare rhodium or bare rhodium catalysts are used in this application for rhodium hydroformylation catalysts which, in contrast to conventional rhodium hydroformylation catalysts, are not modified with ligands, particularly phosphorus-containing ligands, such as phosphine or phosphite ligands, under the hydroformylation conditions. Carbonyl or hydrido ligands are not understood as meaning ligands in this sense. It is assumed in the technical literature (cf. Falbe, page 38 et seq.) that the rhodium compound $HRh(CO)_4$ is the catalytically active rhodium species in the hydroformylation with bare rhodium catalysts, although this has not been definitively proven owing to the many chemical mechanisms taking place side by side in the hydroformylation reaction zone. Merely for the sake of simplicity, we make use of this assumption in this application too, without intending to restrict the scope of protection of the present application if at some time in the future a rhodium species other than the stated one should prove to be the actual catalytically active species. The bare rhodium catalysts form under the conditions of the hydroformylation reaction from rhodium compounds, for example rhodium salts, such as rhodium(III) chloride, rhodium(III) nitrate, rhodium(III) acetate, rhodium(II) acetate, rhodium(III) sulfate or rhodium(III) ammonium chloride, from rhodium chalkogenides, such as rhodium(III) oxide or rhodium(III) sulfide, from salts of oxo acids of rhodium, for example the rhodates, from rhodium carbonyl compounds, such as $Rh_4(CO)_{12}$ and $Rh_6(CO)_{16}$, or from organo rhodium compounds, such as acetonylacetonatorhodium dicarbonyl or cyclooctadienerhodium acetate or chloride, in the presence of $CO/H_2$ mixtures, which are usually referred to as synthesis gas. For carrying out hydroformylations with bare rhodium, reference may be made here, for example, to the following publications: U.S. Pat. No. 4,400,547, DE-A 33 38 340, DE-A 26 04 545, WO 82/03856, Chem. Ber. 102 (1969), 2238, Tetrahedron Lett. 29 (1968), 3261 and Hydrocarbon Process. (1975), 85–86.

However, hydroformylation with bare rhodium also has the disadvantage that, owing to the thermal load during the working up of the hydroformylation product by distillation, the thermally unstable rhodium catalyst (cf. U.S. Pat. No. 4,400,547) undergoes partial decomposition to metallic rhodium, which is deposited on the walls of the reactor and of the pipelines. The deposited rhodium metal cannot be recycled to the hydroformylation reaction since it cannot be converted into the catalytically active rhodium compound under the hydroformylation conditions. The rhodium losses resulting from this chemical behavior of bare rhodium catalysts have to date prevented large-scale industrial use of this process.

DE-A 33 38 340 and U.S. Pat. No. 4,400,547 describe processes for hydroformylation by means of bare rhodium catalysts, in which, in order to prevent the deposition of rhodium, a phosphine or phosphite is added to the reacted mixture from the hydroformylation which, by the formation of phosphine and/or phosphite, complexes, protect the rhodium catalyst from thermal decomposition in the course of working up the discharged hydroformylation mixture by distillation. After the end of the distillation, the rhodium-containing bottom product from the distillation is treated with an oxidizing agent, rhodium being liberated in catalytically active form from the relevant phosphine or phosphite complexes and the phosphide and phosphite ligands being oxidized to the corresponding phosphine oxides and phosphates which do not form rhodium complexes under hydroformylation conditions. The oxidized bottom product from the distillation is then used again as a catalyst for the hydroformylation. The oxidized phosphorus compounds formed in the oxidation generally do not interfere with the hydroformylation but, owing to the process, accumulate in this hydroformylation circulation, making it necessary constantly to remove a bleed stream of this catalyst solution from the hydroformylation circulation and to replace it with fresh catalyst solution. The catalyst solution removed must be subjected to a separate procedure for recovering the rhodium present therein.

WO 82/03856 relates to a process for rendering unmodified, ie. bare, rhodium catalysts heat-stable, in which process the reacted mixture from the hydroformylation reaction is treated with an oxygen-containing gas, with the result that some of the aldehydes formed are oxidized to the corresponding carboxylic acids, which react with the rhodium catalyst in the working up by distillation and form heat-stable rhodium carboxylates, which can again be used as catalysts for the hydroformylation. The disadvantage of this process is the reduction in the yield as a result of the partial oxidation of the aldehydes produced to carboxylic acids. Moreover, this process is limited to hydroformylations in which distillable products are formed: for example, the rhodium catalyst cannot be separated from the hydroformylation product of polyisobutene in this process.

In order to avoid rhodium losses, according to U.S. Pat. No. 3,984,478 a hydroformylation process was developed in which the hydroformylation is carried out in the presence of a phthalocyanine which may be sulfonated. Since some of the rhodium phthalocyanine complexes formed here are sparingly soluble or are soluble only in water but not in the organic hydroformylation medium, the hydroformylation is alternatively carried out in the presence of the solid rhodium phthalocyanines or in a two-phase system with water. However, the coordinate bond between the rhodium and the phthalocyanine in these complexes is very strong so that the rhodium remains bonded to the phthalocyanine even under the hydroformylation conditions. Consequently, the hydroformylation reaction takes place only at the hydroformylation medium/solid phthalocyanine interface or at the interface with the aqueous rhodium phthalocyanine complex solution, with the result that the reaction rate and hence also the space-time yield of the hydroformylation reaction are so low that this process cannot be operated economically.

EP-A 588 525 describes a process for separating rhodium from reacted hydroformylation mixtures by extraction with an aqueous solution of a water-soluble, nitrogen-containing chelating agent, bare rhodium being liberated again under the hydroformylation conditions from the rhodium chelate complex formed in the extraction. A plurality of mixer settler apparatuses are required for carrying out this process on an industrial scale, with the result that this process may be uncompetitively expensive for the preparation of aldehydes which are required only in relatively small amounts.

In the German Patent Application P 43 39 139.7 not yet published at the time of this application, the use of rhodium-containing magnetic pigments as catalysts for the hydroformylation of olefins is proposed.

It is an object of the present invention to provide a process for the hydroformylation of olefins by means of a bare rhodium catalyst, by means of which process, on the one hand, the problems of the deposition of metallic rhodium during working up of the reacted hydroformylation mixture by distillation and the separation of the rhodium catalyst from undistillable, in particular high-boiling or polymeric aldehyde products can be satisfactorily solved. For this purpose, it is intended to find a hydroformylation process in which the precursor compound of the bare rhodium catalyst is bound to a solid carrier and is reversibly dissolved therefrom under the $CO/H_2$ pressure prevailing during the hydroformylation reaction with formation of the bare rhodium or ruthenium catalyst which is homogeneously soluble in the reaction medium of the hydroformylation reaction, and the resulting bare rhodium catalyst should bind to the carrier again after the end of the hydroformylation reaction. The carrier should bind the rhodium catalyst reversibly, ie. this carrier should be capable of being used repeatedly as a rhodium source for the hydroformylation with bare rhodium after the rhodium-laden carrier has been separated from the hydroformylation reaction mixture. A further requirement for the carrier was that it should be capable of being separated from the reacted hydroformylation mixture in a simple manner and virtually without losses; in particular, no expensive filtration steps involving large losses should be required for separating off the carrier laden with noble metal.

We have found that this object is achieved by a process for the preparation of aldehydes and/or alcohols by the hydroformylation of olefins of more than 3 carbon atoms by means of a bare rhodium catalyst dissolved homogeneously in the reaction medium, at superatmospheric pressure and at elevated temperatures, and separation of the rhodium catalyst from the liquid reaction mixture, wherein a magnetizable, inorganic pigment coated with a polymeric binder is used for separating the homogeneously dissolved, bare rhodium catalyst from the hydroformylation medium, and this pigment, after it has been laden with the rhodium contained in the hydroformylation medium, is separated from the liquid hydroformylation medium by applying an external magnetic field.

We have also found a process for the preparation of aldehydes and/or alcohols by the hydroformylation of olefins of more than 3 carbon atoms by means of a bare rhodium catalyst dissolved homogeneously in the reaction medium, at superatmospheric pressure and at elevated temperatures, and separation of the rhodium catalyst from the reaction mixture, wherein the rhodium source used for producing the rhodium catalyst which is homogeneously soluble in the reaction medium is a magnetizable, inorganic pigment which is uncoated or coated with a polymeric binder and contains the rhodium in a reversibly complexed or adsorptively bound form under the conditions of the hydroformylation reaction, and, after the hydroformylation, the magnetizable pigment again laden with the rhodium is separated from the liquid hydroformylation medium by applying an external magnetic field.

The present invention therefore relates to a process for the hydroformylation of olefins using a bare rhodium or ruthenium catalyst which is homogeneously soluble in the reaction medium. According to the invention, a heterogeneous, inorganic, magnetizable pigment which carries bound on its surface the chemical precursor of the bare hydroformylation catalyst serves as the source of this homogeneous hydroformylation catalyst, and this binding of the catalyst precursor to the pigment may be of an adsorptive, ie. physical, nature or a chemical bond, in particular a salt-like bond or a complex bond. Depending on the $CO/H_2$ pressure prevailing in the hydroformylation reactor or, where a precarbonylation stage is included in the hydroformylation plant, on the carbon monoxide or $CO/H_2$ pressure prevailing therein, the catalyst precursor is converted into the bare rhodium catalyst, ceases to be bound to the pigment and passes over in homogeneously dissolved form into the liquid hydroformylation medium where it displays its catalytic activity, whereas the pigment particles now free of the catalyst precursor originally bound thereto remain as catalytically inactive suspension in the hydroformylation medium or can be separated from the hydroformylation medium, depending on the design of the process. After the end of the hydroformylation reaction and/or after the $CO/H_2$ pressure still present in the reacted hydroformylation mixture has been let down, the bare hydroformylation catalyst binds to the magnetic pigment again, the catalyst precursor being formed once again. The magnetic pigment once again laden with the catalyst precursor can be separated from the reacted hydroformylation mixture now freed from the bare hydroformylation catalyst in a simple manner, for example by applying an external magnetic field, and can be used again, in one or more cycles of this type, as a rhodium source for the hydroformylation reaction. In order to carry out the novel process, it is therefore critical that the catalyst precursor bound to the magnetizable pigment, also referred to below as magnetic pigment, can be reversibly detached from this magnetic pigment with formation of the homogeneous catalyst, depending on the $CO/H_2$ or possibly on the CO pressure, reversibly meaning that the homogeneous catalyst binds to the magnetic pigment again at a $CO/H_2$ pressure which is lower than that for detaching it from the magnetic pigment or the $CO/H_2$ pressure required for stabilizing it in the hydroformylation medium, with re-formation of the original catalyst precursor or of another compound suitable as a catalyst precursor.

According to the invention, the magnetic pigment laden with the catalyst precursor compound thus serves as a source of the bare rhodium or ruthenium catalyst to be formed under the reaction conditions of the hydroformylation reaction, whereas, after the end of the hydroformylation reaction and elimination of the $CO/H_2$ pressure, the unladen magnetic pigment performs the function of an adsorbent for the homogeneously dissolved hydroformylation catalyst by taking up said hydroformylation catalyst from the hydroformylation medium and binding said catalyst.

Magnetic pigments which can be used in the novel process may consist of magnetizable particles or of magnetizable particles coated with a binder. Magnetizable particles are to be understood as meaning particles which are magnetic in an external magnetic field. In general, such substances have a saturation magnetization of from 20 to 200, preferably from 30 to 100, $nTm^3/g$, measured in a field of 400 kA/m. The size of the magnetizable particles can be chosen within wide limits. However, if a permanent magnetization of said particles by an external magnetic field is to be avoided, it has proven advantageous to use particles having diameters of from 5 to 1000 nm. Particularly preferred particles are those having diameters of from 5 to 100 nm. The size of particles having such diameters is determined by known methods, for example by electron microscopy, the values being average values for the particular sample.

Specifically, the following substances are suitable as magnetizable cores: iron, nickel, cobalt, chromium dioxide, iron oxides and cubic and hexagonal ferrites, such as ferrites doped with manganese, zinc and cobalt ions and with magnesium, calcium, strontium and barium ions. Such substances are obtainable in a manner known per se, for example by precipitation reactions of corresponding metal salts. Thus, magnetite ($Fe_3O_4$) can be prepared from solutions of $Fe^{2+}/Fe^{3+}$ chlorides by precipitation with sodium hydroxide solution, for example according to DE-A 36 19 746, and chromium dioxide by hydrothermal synthesis, for example according to EP-A 27 640. The metallic cores can also be prepared by thermal decomposition of metal carbonyls, for example according to U.S. Pat. No. 3,228,881. Preferred materials for the magnetizable cores are magnetite and $\gamma\text{-}Fe_2O_3$.

Depending on their diameters, which as a rule are small, the magnetizable cores generally have surface areas of from 1 to 300 $m^2/g$, determined by the BET method (DIN 66 132).

The magnetizable cores can be reacted directly with rhodium compounds which bind adsorptively or chemically to the surface of the core. However, the magnetic core is preferably first coated with a binder. This binder should bind adsorptively or chemically to the magnetizable core and at the same time offer the possibility of binding rhodium compounds adsorptively or, preferably, chemically, so that said compounds are reversibly detached from the coated magnetic pigment with formation of the bare rhodium catalyst under the hydroformylation conditions.

Preferably used binders are organic polymers which are water-soluble or dispersible in water, which means that advantageously at least 1 g of the relevant polymer should dissolve in water or should be capable of being dispersed therein. In order to improve the solubility or the dispersibility of the polymer in water, up 0 to 50, preferably up to 20, in particular up to 10, % by volume of water-soluble organic solvents, such as $C_1$–$C_4$-alcohols, in particular methanol, ethanol, propanol, isopropanol or tert-butanol, water-soluble ethers, for example tetrahydrofuran, dioxane or dimethoxyethane, water-soluble ketones, for example acetone, water-soluble amides, for example N,N-dimethylformamide or N-methylpyrrolidone, or water-soluble sulfoxides, for example dimethylsulfoxide, may also be mixed with the water.

Polymeric binders which are preferably used for coating the magnetic pigments which can be used according to the invention are those which contain polar functional groups, for example carboxyl, sulfo, amido, phospho or amino groups or other nitrogen-containing groups capable of forming coordinate bonds. These binders may be homo- or copolymers and may be composed of monomers such as unsaturated carboxylic acids, eg. acrylic acid, methacrylic acid and/or maleic acid, unsaturated sulfonic acids, eg. vinylsulfonic acid and/or styrenesulfonic acid, unsaturated phosphonic acids, eg. vinylphosphonic acid, unsaturated anhydrides, eg. maleic anhydride, unsaturated amines, eg. vinylamine, unsaturated amides, eg. acrylamide and/or vinylpyrrolidone, and/or other unsaturated, nitrogen-containing monomers, eg. vinylpyrrolidine, vinylpyridine and/or vinylbipyridine. These polymers, in particular the nitrogen-containing, polymeric binders, may be partially oxidized; for example, polyvinylpyridine may be used as a binder in which from 0 to 90%, preferably from 25 to 75%, of the nitrogen atoms are oxidized. The polymeric binders may additionally be composed of comonomers other than the abovementioned ones, for example ethylene, propylene or styrene, but the amount of the abovementioned monomers carrying polar groups in the polymer of the binder is preferably at least 50% by weight.

Polymeric binders which are suitable for the purpose of the novel process are, for example, polyacrylates, polymethacrylates, polyvinylpyrrolidone, poly(2-vinylpyridine), 2-vinylpyridine/styrene copolymers, polyacrylates, polyimides, polyamides and polyurethanes.

Such homo- and copolymers are commercially available or can be prepared by methods known per se, for example by free radical polymerization. Particularly preferred binders are polyvinylpyridines, in particular poly(2-vinylpyridine) and poly(4-vinylpyridine), having an average molecular weight of from 1,000 to 1,000,000 Dalton. These polyvinylpyridines may contain up to 20% by weight of other comonomers, for example styrene, ethylene or propylene, incorporated in the polymer. Such polyvinylpyridines are commercially available.

The amount of the binder to be applied to the magnetic pigment is advantageously such that at least a monolayer of the binder can form on the magnetizable pigment particles. For this purpose, from 0.1 to 5 mg of the polymer serving as the binder are generally required per square meter of surface of the magnetic pigment.

In order to coat the magnetizable pigment with the binder, the magnetic pigment is advantageously suspended in water or in a mixture of water with a water-soluble organic solvent, and the binder, advantageously in the form of a solution or suspension in water or in a mixture of water and a water-soluble organic solvent, is added to this suspension, and this mixture is stirred at in general from 10° to 100° C., in general for from 10 to 60 minutes. Shorter or longer stirring times may also be selected. The magnetic pigment is then separated from the supernatent solution or suspension, for example by filtration, centrifuging or, preferably, separation by application of an external magnetic field.

To enable the magnetic pigments prepared in this manner to serve as a source of the homogeneous hydroformylation catalyst in the novel process, they must first be laden with the catalyst precursor. The magnetic pigment, preferably the coated magnetic pigment, is particularly preferably laden with rhodium compounds. However, precursor compounds of other metals having hydroformylation activity, such as ruthenium or cobalt, may also be applied to the magnetic pigment. The application of rhodium compounds as precursor compounds for the bare, homogeneous hydroformylation catalyst proves to be particularly advantageous for the novel process.

In order to apply the catalyst precursor to the uncoated magnetic pigment or preferably to the magnetic pigment coated with the binder, the relevant metal compounds, ie. cobalt, ruthenium or rhodium compounds, particularly preferably rhodium compounds, dissolved or suspended in a polar or nonpolar solvent, can be brought into contact with the coated or uncoated magnetic pigment, the metal compounds being adsorptively or preferably, in the case of coated magnetic pigments, chemically bound to the magnetic pigment.

A large number of metal compounds, in particular rhodium compounds, are suitable for application as a catalyst precursor to the magnetic pigment, in particular metal salts, such as rhodium(III) nitrate, rhodium(III) acetate, rhodium halides, in particular rhodium chlorides, such as rhodium(III) chloride, rhodium(II) acetate, rhodium(III) sulfate or rhodium(III) ammonium chloride, salts of oxo acids of rhodium, such as the rhodates, rhodium carbonyl compounds, such as $Rh_4(CO)_{12}$ and $Rh_6(CO)_{16}$, or organo rhodium compounds, Such as acetonylacetonatorhodium dicarbonyl, cyclooctadiene rhodium acetate or chloride and other rhodium-olefin complexes. Because they are readily available commercially, rhodium nitrate and rhodium acetate are preferably used for loading the magnetic pigment for the first time. According to the invention, the bare rhodium catalyst dissolved homogeneously in the hydroformylation medium is deposited on the magnetic pigment in the course of separating this catalyst from the hydroformylation mixture, and the chemical structure of said catalyst is changed as a result of forming salt-like or coordinate chemical bonds with the functional groups of the binder and said catalyst is converted back into the catalyst precursor.

It is of course also possible to carry out the hydroformylation with bare rhodium in a conventional manner and to use the magnetic pigments, which can be used according to the invention, for separating off the homogeneously dissolved, bare rhodium catalyst, ie. to use a reacted rhodium-containing hydroformylation mixture as a starting material for the initial loading of the magnetic pigment with rhodium. The rhodium-containing magnetic pigments produced in this manner can then be further used as a rhodium source, as described, in hydroformylation reactions with bare rhodium as a catalyst.

Depending on the type of rhodium compound, water or polar or nonpolar organic solvents may be used as solvents for applying the rhodium compounds to the magnetic pigment. Water and polar organic solvents, such as $C_1$–$C_4$-alcohols, in particular methanol, ethanol, propanol, isopropanol and tert-butanol, water-soluble ethers, such as tetrahydrofuran, dioxane or dimethoxyethane, pyridine, N-methylpyrrolidone, dimethylformamide, dimethyl sulfoxide, acetone, etc., or mixtures of these solvents with water are preferably used as solvents for the rhodium compounds for the application of rhodium salts where the magnetic pigment is treated for the first time with salt-like or other water-soluble rhodium compounds.

Nonpolar organic solvents, for example the olefins to be hydroformylated, and aromatic hydrocarbons, such as benzene, toluene or xylene, preferably serve as solvents for nonpolar organometallic rhodium compounds, such as rhodium carbonyl compounds or rhodium-olefin complexes, when the magnetic pigment is laden with such rhodium compounds. According to the invention, the hydroformylation mixture formed in the course of the novel process and comprising the olefin to be hydroformylated, the aldehydes formed therefrom and their relatively high molecular weight condensation products is in practice the solvent for a further application of the bare rhodium catalyst to the magnetic pigment. Mixtures of high-boiling condensation products of aldehydes which are formed as byproducts in the hydroformylation and are commercially available, for example under the name Texanol® can furthermore serve as solvents.

The rhodium compound can be applied to the magnetic pigment, for example, by stirring a suspension of the magnetic pigment in the solvent containing the particular rhodium compound. This may preferably be effected at room temperature, but temperatures of from 0° C. to the boiling point of the solvent used, advantageously temperatures of up to 100° C., may also be selected. The time for which the rhodium-containing solvent is in contact with the magnetic pigment is advantageously about 5 minutes, but of course longer contact times may also be used. Depending on the type of binder present on the magnetic pigment and the type and number of functional groups present therein, in general from 0.05 to 20% by weight, based on the weight of the inorganic core of the magnetic pigment, and calculated as Rh, of rhodium are bound to the magnetic pigment. On binding to the functional groups of the binder applied to the magnetic pigment, the rhodium compound used generally undergoes a chemical transformation by interacting chemically with these groups. It is also possible, for example, to deposit colloidal rhodium adsorptively, ie. by physical interaction, on the uncoated magnetic pigment, but the rhodium compounds are preferably fixed by chemical interactions to a magnetic pigment coated with one of the stated binders.

The rhodium-containing magnetic pigments thus obtained serve as a rhodium source in the novel hydroformylation process. They can be used at up to 250° C. and are pressure-stable, depending on the type of binder used.

The hydroformylation is carried out in general at from 60° to 180° C., preferably from 80° to 140° C., particularly preferably from 90° to 130° C., and at in general from 50 to 1,000 bar. Synthesis gas is required as a reagent for the hydroformylation. Synthesis gas is understood as meaning a $CO/H_2$ mixture in which carbon monoxide and hydrogen are generally present in a molar ratio of from 1:5 to 5:1, preferably from 4:6 to 6:4. Otherwise, the hydroformylation is carried out under conditions as usually used in hydroformylations with bare rhodium and as described, for example, in the literature cited at the outset and relating to hydroformylation with bare rhodium. If desired, the synthesis gas may also be diluted with gases which are inert under the reaction conditions, such as nitrogen, argon or saturated, gaseous hydrocarbons.

The product ratio alcohol/aldehyde in the reacted hydroformylation mixture may be influenced depending on the pressure and temperature conditions used in the hydroformylation stage and on the composition of the synthesis gas. For example, in the hydroformylation of trimeric propylene, a molar aldehyde/alcohol ratio of 93/7 is obtained in each case with the same synthesis gas compositions —$CO/H_2$ molar ratio 50/50, 40/60 and 60/40—at 130° C. and 280 bar. When the temperature is increased from 130° C. to 150° C., the molar aldehyde/alcohol ratio in the reacted hydroformylation mixture changes as a function of the synthesis gas composition—$CO/H_2$ molar ratio 50/50, 40/60 and 60/40—to 76/24, 67/33 and 82/18 respectively.

The hydroformylation can be carried out in the presence or absence of organic solvents. The use of organic solvents is particularly advantageous, especially in the hydroformylation of long-chain or polymeric olefins. The solvents usually used in the hydroformylation process may be used as solvents, for example high-boiling aromatic and aliphatic hydrocarbons or high-boiling aldehyde condensates which are formed as byproducts as a result of the condensation of the aldehyde products in the course of the hydroformylation reaction.

Experiments have shown that the rhodium catalyst precursor bound to the magnetic pigment becomes detached from the magnetic pigment under the conditions of the hydroformylation reaction and goes into solution in the form of the bare rhodium catalyst, the latter catalyzing the hydroformylation reaction. The experimental results also indicate that the amount of homogeneous rhodium catalyst which goes into solution and is present in the hydroformylation medium during the hydroformylation reaction also appears to be dependent on the amount of olefin present in the hydroformylation medium. Under the reaction conditions and depending on the presence and concentration of the reactants $CO/H_2$ and olefin, a chemical equilibrium is evidently established in the reactor between the catalyst precursor fixed on the magnetic pigment and the rhodium catalyst present homogeneously in the reaction medium, with the result that, when the reactants hydrogen and in particular carbon monoxide and olefin are in short supply, for example due to their consumption in the course of a batchwise reaction or due to the $CO/H_2$ pressure in the reactor being let down in order to terminate the reaction, the rhodium catalyst present homogeneously in the reaction medium binds again to the magnetic pigment so that, at the end of the hydroformylation, the liquid hydroformylation mixture is virtually free of rhodium and the bare rhodium catalyst dissolved homogeneously in the reaction medium during the hydroformylation is once again virtually completely bound to the magnetic pigment.

The magnetic pigment once again laden with rhodium can be separated from the reacted liquid hydroformylation mixture after the end of the reaction in a simple and gentle manner and virtually without loss by applying an external magnetic field. This can be effected, for example, by bringing the hydroformylation medium into contact with a permanent magnet, onto which the rhodium-laden magnetic pigment is deposited, or preferably by switching on an electromagnet, the rhodium-laden magnetic pigment being deposited on the magnet and being held firmly by it.

Magnetic filters may also be used for separating the magnetic pigment from the reacted hydroformylation mixture, for example a magnetic filter as described in Journal of Magnetism and Magnetic Materials 85 (1990), 285.

The reacted hydroformylation mixture freed with the aid of the magnetic pigment from the rhodium catalyst dissolved therein can be worked up in a conventional manner, for example by distillation, preferably after the magnetic pigment has been physically separated off. The rhodium-laden magnetic pigment which has been separated off can advantageously then be reused as a rhodium source in the hydroformylation. Since the magnetic pigments which can be used according to the invention as a rhodium source generally have a residual induction of less than 40, preferably less than 20, $nTm^3/g$, measured using a vibrating sample magnetometer, they do not remain permanently magnetic after the magnet has been removed or switched off, and they therefore retain their finely divided pigment structure and do not agglomerate. This considerably facilitates the recycling and reuse of the rhodium-laden magnetic pigments in subsequent hydroformylations and ensures the distribution of the pigment particles in the hydroformylation medium as well as the retention of the optimum surface of the magnetic pigment. Owing to their finely divided nature, the magnetic pigment particles remain suspended, during the hydroformylation procedure, in the hydroformylation medium which is stirred or otherwise kept in motion, for example by passing through a $CO/H_2$ or inert gas stream, as long as no external magnetic field is applied. After a magnetic field is switched on, the magnetic pigment completely separates out from the hydroformylation liquid within a short time.

The amount of rhodium-laden magnetic pigment added to the hydroformylation reactor as a rhodium source per volume unit of hydroformylation mixture may be varied within wide limits and is dependent on the amount of rhodium applied to the magnetic pigment. Of course, in the case of a larger amount of magnetic pigment and hence a larger amount of available rhodium catalyst, the space-time yield in the hydroformylation reactor increases and does so as a function of the concentration of the hydroformylation reactants hydrogen, carbon monoxide and olefin, which result in removal of the rhodium from the magnetic pigment and the formation of the bare hydroformylation catalyst. As a rule, the magnetic pigment is added to the hydroformylation medium in an amount such that from 10 to 1,000, preferably from 50 to 200, ppm by weight, calculated as Rh, of rhodium are available per kg of olefin to be hydroformylated. Advantageously, the optimum amount of magnetic pigment to be added is optimized in a preliminary experiment for the particular reactor used and the olefin to be hydroformylated.

The novel hydroformylation process can be carried out batchwise, semicontinuously or continuously. In the batchwise procedure, it is possible to use hydroformylation reactors which are known per se and which, if desired, may be additionally equipped at a suitable point, for example at the bottom of the reactor, with an electromagnet for separating off the magnetic pigment. After the end of the reaction, the magnetic pigment with the rhodium once again fixed thereon can be separated off from the hydroformylation liquid by switching on the electromagnet, and said hydroformylation liquid can then be discharged from the reactor. The magnetic pigment can be separated off after letting down the reactor or at the pressure prevailing in the reactor. When the reactor is refilled with reaction medium, the magnetic field is switched off and the magnetic pigment is suspended again in the hydroformylation liquid so that the homogeneous, bare rhodium catalyst can form again therefrom under the reaction conditions of the hydroformylation.

In order to separate off the magnetic pigment, the reacted hydroformylation mixture containing the magnetic pigment in suspension can be passed through a magnetic filter before or after being let down. The magnetic pigment particles are retained in the magnetic filter. After the reactor has been emptied, fresh olefin can advantageously be pumped into the reactor in the opposite direction through the magnetic filter after the magnetic field has been switched off, and the magnetic pigment is thus washed back into the reactor.

It is also possible to let down the pigment-containing reacted hydroformylation mixture from the hydroformylation reactor into a container or a second hydroformylation reactor and to separate off the magnetic pigment there by applying a magnetic field. The magnetic pigment can then be suspended in fresh olefin and recycled to the hydroformylation reactor or the subsequent hydroformylation can be carried out in the second hydroformylation reactor and its reacted hydroformylation mixture let down into the first hydroformylation reactor. The latter procedure can also be operated continuously.

The novel process is particularly suitable for the hydroformylation of olefins of more than 3, preferably more than 7, carbon atoms, in particular for the hydroformylation of $C_7$–$C_{20}$-olefins which may be straight-chain or branched and may contain α-olefinic and/or internal double bonds, eg. 1-octene, 1-dodecene, trimeric and tetrameric propylene or dimeric, trimeric and tetrameric butylene. Unsaturated oligomers of other olefins may also be hydroformylated, as may cooligomers of different olefins. The aldehydes formed from these olefins are used, for example, as intermediates for the preparation of plasticizer alcohols and surfactants, which can be produced therefrom in a conventional manner by hydrogenation. The olefins used for the hydroformylation may be obtained, for example, by acid-catalyzed elimination of water from the corresponding fatty alcohols or by many other industrial processes, as described, for example, in Weissermel, Arpe: Industrielle Organische Chemie, pages 67–86, Verlag Chemie, Weinheim, 1978.

The novel process is also particularly suitable for the hydroformylation of polymeric olefins, for example low molecular weight polyisobutene, low molecular weight polybutadiene or low molecular weight 1,3-butadiene/isobutene or butene copolymers. Low molecular weight polymers are understood as meaning in particular polymers having molecular weights of from 500 to 5,000 Dalton. However, higher molecular weight, unsaturated polymers may also be hydroformylated. The only precondition here is that they are soluble in the hydroformylation medium. The hydroformylation products of these polymeric olefins, in particular those of low molecular weight polyisobutene, can be converted by reductive amination, for example by the process of EP-A 244 616, into the corresponding amines, which are used as fuel additives. Low molecular weight polyisobutene is obtainable, for example, by the process of EP-A 145 235, and low molecular weight isobutene-1,3-butadiene copolymers can be obtained, for example, by the process of Patent Application WO 94/20554.

The novel process is suitable in practice for the preparation of all aldehydes which are obtainable by the hydroformylation of olefins. It should be pointed out in particular that, for example, substituted olefins, which generally may carry 1 or 2 substituents, preferably one substituent, can also be hydroformylated by the novel process. For example, unsaturated, aliphatic carboxylates, acetals, alcohols, ethers, aldehydes, ketones, amines and amides may be hydroformylated by the novel process. Important substituted starting olefins of this type are, for example, methacrylates, dicyclopentadiene, vinyl and allyl ether, in particular correspondingly substituted derivatives of unsaturated fatty acids, for example the esters of oleic, linoleic, linolenic, ricinoleic or erucic acid. The aldehydes obtainable from these olefinic raw materials by hydroformylation are likewise starting materials for the preparation of readily biodegradable detergent substances.

As stated above, a mixture of the aldehyde derived from the olefin used by hydroformylation and the corresponding alcohol formed therefrom as a result of the hydrogenation activity of the rhodium catalyst is formed as the hydroformylation product. If desired, the alcohol content of the hydroformylation product can be increased by the above-mentioned changes to the reaction conditions. The alcohols thus formed likewise serve as plasticizers or surfactants or as starting material for the preparation of these products.

EXAMPLES

A. Production of the Magnetizable Particles

The magnetite was produced according to DE-A 35 00 471 by precipitation reaction in which a stoichiometric solution of $Fe^{2+}$/$Fe^{3+}$ chlorides in water was added dropwise to a solution of sodium hydroxide in water. The precipitated magnetite was filtered and was washed chloride-free. A filter cake having a magnetite content of 24% by weight was formed. The dried pigment was characterized by the following measured values: the BET surface area was measured according to DIN 66 132. It was 59 $m^2$/g. The magnetic properties were determined using a vibrating sample magnetometer. The saturation magnetization was 79 $nTm^3$/g., measured in a field of 400 kA/m.

B. Coating of the Magnetite with Polymer

A solution of 10 g of poly-4-vinylpyridine/poly-4-vinylpyridine-N-oxide having a degree of oxidation of 67% and a K value (1% strength in 5% strength NaCl; determined according to H. Fikentscher, Cellulose-Chemie 13 (1932), 58–64 and 71–74) of 14.2 (prepared according to WO 94/20549) in 250 g of water was brought to pH 9.6 by adding 37 g of 5% strength NaOH solution. This polymer solution was added to 100 g of the filter cake described in Example A and stirred in, a further 400 g of water were added and homogenization was then effected for one hour using an Ultra-Turrax® dispersing apparatus (manufacturer: Janke & Kunkel, Staufen/Breisgau, Germany) while blanketing with nitrogen and cooling with ice. The pH of the mixture was measured as 6.5, which was increased to pH 7.6 by adding 49 g of 5% strength NaOH solution.

C. Preparation of the Novel Catalyst

A solution of 280 mg of $Rh(NO_3)_3$ in 30 g of water was added to the suspension described under B. Dispersing was carried out for a further 15 minutes. A pH of 7.3 was measured. The suspension was then dried at 80° C. in a rotary evaporator and under reduced pressure from a water pump and finally ground to dust. The magnetic dust was investigated: the BET surface area was 30 $m^2$/g. The saturation magnetization was 79 $nTm^3$/g, measured in a field of 400 kA/m.

D. Testing of the Catalytic Properties 100 g of octene N and 11 g of the rhodium-polymer-magnetite catalyst obtained according to Example C (corresponding to 100 ppm of Rh, based on the olefin) were treated with $CO/H_2$ at 100 bar ($CO/H_2$ molar ratio 1:1) in an autoclave. The mixture was then heated to 130° C. and the $CO/H_2$ pressure increased to 280 bar. The pressure and temperature were kept constant for 3 hours. After the autoclave had been cooled to room temperature and let down, the magnetic pigment was deposited on 2 magnetic bars (Vacodym® 370 HR; manufacturer: Vacuumschmelze GmbH). The pigment-free product mixture was analyzed. The formation of aldehyde in a yield of 33% was observed. The rhodium concentration in the pigment-free product mixture was determined by means of atomic absorption spectrometry. It was less than 0.1 ppm by weight.

E. Repeated Testing of the Catalytic Properties

The moist pigment of Example D which had been deposited on the magnetic bars was separated from the liquid reaction product by decanting., the magnet was removed and a further 100 g of octene N were then added. The hydroformylation was repeated as in Example D. After the autoclave had been let down, the magnetic pigment was again deposited on two magnetic bars. The pigment-free product mixture was analyzed. The formation of aldehyde in a yield of 29% was observed. The rhodium concentration in the pigment-free product mixture was less than 0.1 ppm by weight.

F. Repeated Testing of the Catalytic Properties

The moist pigment of Example E which had been deposited on the magnetic bars was separated from the liquid reaction product by decanting, the magnet was removed and a further 100 g of octene N were then added. The hydroformylation was repeated as in Example D. After the autoclave had been let down, the magnetic pigment was again deposited on the magnetic bars. The pigment-free product mixture was analyzed. The formation of aldehyde in a yield of 34% was observed. A rhodium concentration of 0.1 ppm by weight was measured in the pigment-free product mixture.

G. Preparation of Dry Polymer-coated Magnetite

A suspension was prepared as in Example B and was dried at 80° C. in a rotary evaporator and under reduced pressure from a water pump and ground to dust. The magnetic dust was heated for one week at 120° C. in air and then investigated. The BET surface area was 37 m²/g, which indicates that no melting of the pigment has occurred.

H. Preparation of a Rhodium-containing Organic Solution 1.023 g of octene N and 530 mg of acetylacetonatorhodium(i) dicarbonyl (corresponding to 200 ppm, based on the olefin, of Rh) were treated with $CO/H_2$ at 100 bar ($CO/H_2$ molar ratio 1:1) in an autoclave. The mixture was then heated to 130° C. and the $CO/H_2$ pressure increased to 280 bar. The pressure and temperature were kept constant for 4 hours. After the autoclave had been cooled to room temperature and let down, the rhodium concentration in the product mixture was measured: it was 130 ppm by weight.

I. Preparation of the Novel Catalyst

For the preparation of the novel catalyst, 857 g of the solution from Example H were heated to 80° C. 80 g of magnetic pigment from Example G were added and stirring was carried out for 3 hours at 80° C. After cooling, the magnetic pigment was deposited on two magnetic bars. The supernatent solution was decanted and investigated. The rhodium concentration was 3 ppm by weight, which indicates that more than 97% of the rhodium had been separated off. The moist magnetic pigment was freed from solvent residues at from 130° to 150° C. under reduced pressure and ground to dust in an impact mill. The dust was investigated: the BET surface area was 32 m²/g, the saturation magnetization was 65 nTm³/g, measured in a field of 400 kA/m, and its rhodium content was 1,400 ppm by weight.

J. Testing of the Catalytic Properties 100 g of octene N and 7.1 g of the rhodium-polymer-magnetite catalyst obtained according to Example I (corresponding to 100 ppm, based on the olefin, of Rh) were treated with $CO/H_2$ at 100 bar (in a molar ratio of 1:1) in an autoclave. The mixture was then heated to 130° C. and the $CO/H_2$ pressure increased to 280 bar. The pressure and temperature were kept constant for 3 hours. After the autoclave had been cooled to room temperature and let down, the magnetic pigment was deposited on 2 magnetic bars (Vacodym® 370 HR). The pigment-free product mixture was analyzed. The formation of aldehyde in a yield of 58% was observed. The rhodium concentration of the pigment-free product mixture was 0.5 ppm by weight.

K. Repeated Testing of the Catalytic Properties

The moist pigment of Example J which had been deposited on the magnetic bars was separated from the liquid reaction product by decanting, the magnet was removed and a further 100 g of octene N were then added. The hydroformylation was repeated as in Example J. After the autoclave had been cooled to room temperature and let down, the magnetic pigment was again deposited on two magnetic bars. The pigment-free product mixture was analyzed. The formation of aldehyde in a yield of 59% was observed. The rhodium Concentration of the pigment-free product mixture was 0.3 ppm by weight.

L. Repeated Testing of the Catalytic Properties

The moist pigment of Example K which had been deposited on the magnetic bars was separated from the liquid reaction product by decanting, the magnet was removed and a further 100 g of octene N were then added. The hydroformylation was repeated as in Example J. After the autoclave had been cooled to room temperature and let down, the magnetic pigment was again deposited on the magnetic bars. The pigment-free product mixture was analyzed. The formation of aldehyde in a yield of 67% was observed. A rhodium concentration of 0.3 ppm by weight was measured in the pigment-free product mixture.

M. Testing of the Catalytic Properties 130 g of a mixture of polyisobutene (average molecular weight about 1,000) with a $C_{10}$–$C_{15}$-paraffin mixture, volume ratio 1:1 (BASF commercial product Glissopal® ES 3250) and 5 g of the rhodium-polymer-magnetite catalyst obtained according to Example I (corresponding to 52 ppm by weight, based on the mixture, of Rh) were treated with $CO/H_2$ at 100 bar ($CH/H_2$ molar ratio 1:1) in an autoclave. The mixture was then heated to 130° C. and the $CO/H_2$ pressure increased to 280 bar. The pressure and temperature were kept constant for 5 hours. After the autoclave had been cooled to room temperature and let down, the magnetic pigment was deposited on 2 magnetic rods.(Vacodym® 370 HR). The pigment-free product mixture was freed from the paraffin solvent by distillation at 150° C. and 13 mbar and then analyzed: the rhodium concentration was 3 ppm by weight. A conversion of 31% was calculated from the CO number of 17 mg per g.

N. Coating of Magnetite with Polymer

A solution of 10 g of vinylpyrrolidone/vinylimidazole copolymer (50/50, K value=17.6) in 500 g of water was added to 237 g of filter cake containing 100 g of magnetite as in Example A and homogenization was carried out for one hour with an Ultra Turrax® dispersing apparatus while blanketing with nitrogen and cooling with ice. A pH of 7.3 was measured in the mixture after the addition of 8 g of 5% strength NaOH solution. The suspension was dried at 90° C. in a rotary evaporator and under reduced pressure from a water pump and finally ground to dust. The magnetic dust was investigated: the BET surface area was 44 m$^2$/g. The saturation magnetization, measured in a field of 400 kA/m, was 79 nTm$^3$/g and the residual induction was 7 nTm$^3$/g.

O. Preparation of the Novel Catalyst

A rhodium-containing organic solution was prepared according to Example H by reducing the amount of rhodium so that the rhodium concentration was 70 ppm. 200 g of this solution were stirred with 10 g of magnetic dust from Example N for one hour at room temperature (ie. 23±2° C.). The magnetic dust was deposited on a bar magnet and the rhodium concentration in the supernatent clear solution was measured. It was only 7 ppm by weight, indicating the deposition of 12.6 mg of rhodium onto the magnetic pigment.

Determination of the CO Number

The CO number was determined alkalimetrically. Procedure: The sample dissolved in toluene was oximated for one hour at 85° C. and at a pH of 2.5 with an aqueous hydroxylamine hydrochloride solution. According to the definition, it is assumed that one molecule of hydrochloric acid is liberated per carbonyl (C=O) group. After cooling, the solution was titrated potentiometrically with an NaOH standard solution.

Octene N

Product from the dimerization of butene by the IFP Dimersol process (cf. Weissermel, Arpe: Industrielle Organische Chemie; 2nd edition, page 82, Verlag Chemie, weinheim 1978).

We claim:

1. A process for the preparation of aldehydes or alcohols by the hydroformylation of olefins of more than 3 carbon atoms by means of a bare rhodium catalyst dissolved homogeneously in the reaction medium, at superatmospheric pressure and at elevated temperatures, and separation of the rhodium catalyst from the liquid reaction mixture, wherein a magnetizable, inorganic pigment coated with a polymeric binder is used for separating the homogeneously dissolved, bare rhodium catalyst from the hydroformylation medium, and this pigment, after it has been laden with the rhodium contained in the hydroformylation medium, is separated from the liquid hydroformylation medium by applying an external magnetic field.

2. A process as claimed in claim 1, wherein the magnetizable pigment used is a magnetizable pigment having a residual induction of less than 40 nTm$^3$/g.

3. A process as claimed in claim 1, wherein the magnetizable pigment used is finely divided iron, nickel, cobalt, chromium dioxide, iron oxides, cubic or hexagonal ferrites or ferrites doped with manganese, zinc, cobalt, magnesium, calcium, strontium or barium ions.

4. A process as claimed of claim 1, wherein the magnetizable pigment used is one which has been coated with a polymeric binder containing carboxyl, sulfo, phospho, amido or amino groups or other nitrogen-containing groups capable of coordination with rhodium compounds.

5. A process as claimed in claim 4, wherein the magnetizable pigment used is one which has been coated with a polyacrylate, polymethacrylate, polyacrylamide, polyvinylpyrrolidone, polyvinylpyridine, partially oxidized polyvinylpyridine or vinylpyrrolidone/vinylimidazole copolymer as the polymeric binder.

6. A process for the preparation of aldehydes or alcohols by the hydroformylation of olefins of more than 3 carbon atoms by means of a bare rhodium catalyst dissolved homogeneously in the reaction medium, at superatmospheric pressure and at elevated temperatures, and separation of the rhodium catalyst from the reaction mixture, wherein the rhodium source used for producing the rhodium catalyst which is homogeneously soluble in the reaction medium is a magnetizable, inorganic pigment which is uncoated or coated with a polymeric binder and contains the rhodium in a reversibly complexed or adsorptively bound form under the conditions of the hydroformylation reaction, and, after the hydroformylation, the magnetizable pigment again laden with the rhodium is separated from the liquid hydroformylation medium by applying an external magnetic field.

7. A process as claimed in claim 6, wherein a magnetizable, inorganic pigment coated with a polymeric binder is used.

8. A process as claimed in claim 6, wherein the magnetizable pigment used is a magnetizable pigment having a residual induction of less than 40 nTm$^3$/g.

9. A process as claimed in claim 6, wherein the magnetizable pigment used is finely divided iron, nickel, cobalt, chromium dioxide, iron oxide, cubic or hexagonal ferrite or ferrite doped with manganese, zinc, cobalt, magnesium, calcium, strontium or barium ions.

10. A process as claimed in claim 6, wherein the magnetizable pigment used is one which has been coated with a polymeric binder containing carboxyl, sulfo, phospho, amido or amino groups or other nitrogen-containing groups capable of coordination with rhodium compounds.

11. A process as claimed in claim 6, wherein the magnetizable pigment used is one which has been coated with a polyacrylate, polymethacrylate, polyacrylamide, polyvinylpyrrolidone, polyvinylpyridine, partially oxidized polyvinylpyridine or vinylpyrrolidone/vinylimidazole copolymer.

* * * * *